United States Patent
Airey et al.

(10) Patent No.: US 7,614,285 B2
(45) Date of Patent: Nov. 10, 2009

(54) DYNAMIC RECIPROCATING-BOB RHEOMETRY

(75) Inventors: Daniel A. Airey, Woburn, MA (US); Jonathan T. Cole, Sudbury, MA (US)

(73) Assignee: Cambridge Viscosity, Inc., Medford, MA (US)

( * ) Notice: Subject to any disclaimer, the term of this patent is extended or adjusted under 35 U.S.C. 154(b) by 308 days.

(21) Appl. No.: 11/691,554

(22) Filed: Mar. 27, 2007

(65) Prior Publication Data
US 2008/0236254 A1    Oct. 2, 2008

(51) Int. Cl.
    *G01N 11/10*    (2006.01)
(52) U.S. Cl. ...................................... 73/54.23
(58) Field of Classification Search ............... 73/54.23, 73/54.01, 54.41
    See application file for complete search history.

(56) References Cited

U.S. PATENT DOCUMENTS

| | | | |
|---|---|---|---|
| 4,627,272 A | 12/1986 | Wright | |
| 4,864,849 A | 9/1989 | Wright | |
| 5,025,656 A | 6/1991 | Wright | |
| 5,327,778 A * | 7/1994 | Park | 73/54.21 |
| 5,394,739 A | 3/1995 | Garvey, III et al. | |
| 5,698,773 A * | 12/1997 | Blom et al. | 73/54.18 |
| 6,584,831 B1 * | 7/2003 | Kasameyer et al. | 73/54.23 |
| 2003/0115936 A1 | 6/2003 | Kasameyer et al. | |

OTHER PUBLICATIONS

International Search Report and Written Opinion for PCT/US08/55794.

* cited by examiner

*Primary Examiner*—Hezron Williams
*Assistant Examiner*—Nathaniel Kolb
(74) *Attorney, Agent, or Firm*—Foley Hoag LLP

(57) ABSTRACT

A sensor for making rheological measurements takes the form of a ferromagnetic bob alternately driven through a sample fluid in opposite directions by magnetic force from two alternately driven coils. The bob's position affects the mutual inductance between the coils, so it can be inferred by sensing the signal that current flowing in one coil induces in the other, and rheological properties are determined from the relationships among the bob's motion, the coil current, and the sensor geometry. Some such measurements' accuracies are enhanced by computing bob acceleration and suppressing inertial effects thereby detected.

28 Claims, 12 Drawing Sheets

DYNAMIC RECIPROCATING-BOB RHEOMETRY

BACKGROUND OF THE INVENTION

1. Field of the Invention

The present invention concerns measurements of viscosity and related fluid properties. It finds particular application in uses of sensors that employ reciprocating magnetically driven bobs.

2. Background Information

Fluids' rheological characteristics have been subjects of study for well over a century, and measurements have for nearly as long been made in laboratories routinely to characterize fluids that have been newly developed or encountered. Instruments used for this purpose usually employ some rotated cylindrical member to subject the fluid of interest to shearing, and various rheological properties are inferred from the fluid's resistance to such shearing at various cylinder speeds. Examples of the characteristics that such instruments determine are whether the fluid is Newtonian, what its shear sensitivity is, what its relationship is between shear stress and shear rate, what its yield stress is, and whether it is complex in the sense that its viscosity drifts with extended exposure to shearing.

Such methods of rheological-characteristic determination have proved quite effective and accurate, but there are a range of applications in which they have not proved very practical. Some research, for example, involves screening large numbers of fluids that are expensive to formulate. The expense of some such fluids has tended to dissuade researchers from screening them.

SUMMARY OF THE INVENTION

But I have recognized that such a barrier is greatly lowered by applying to such rheological measurements a type of sensor apparatus that has been used for decades to perform industrial viscosity measurements.

That type of sensor is exemplified by the device described in U.S. Pat. No. 4,864,849 to Wright. A ferromagnetic bob is driven alternately in opposite directions by two coils through a bob channel that contains the fluid to be measured. Drive current flowing through one of the coils draws the ferromagnetic bob through the path in one direction. The bob's movement causes a change in the mutual inductance between the two coils and therefore in the amplitude of the signal induced in the other of the coils by an AC component in the first coil's drive current. By monitoring that signal's amplitude, circuitry can determine when the bob has reached a predetermined point in its travel. The circuitry can then switch the coils' functions so that the erstwhile driving coil becomes the sensor coil and vice versa, and the bob therefore switches direction. Since the geometry of the bob and the channel within which it travels are known, as is the force with which the coils drive the bob through that channel, the fluid's viscosity can be computed from the time taken by the bob to traverse the bob path.

Such sensors' low cost, ruggedness, and simplicity have made it practical to monitor the properties of fluids as diverse as printing ink, hydraulic fluid, and paint so as, for example, to enable their characteristics to be adjusted automatically or to trigger automatic replacement at economically optimum intervals. But I have now recognized that another characteristic of this type of sensor makes additionally applying it to other rheological measurements particularly advantageous: it can be employed on samples small enough to make it practical to screen fluids that are too expensive to screen with conventional laboratory instruments.

Additionally, I have made an advance in the way in which this sensor type of sensor makes measurements. Conventionally, the bob velocity on which computations of viscosity are based is determined by measuring the time required for the bob to reach a predetermined position as indicated, for example, by the detection-coil amplitude's falling to some predetermined fraction of its peak value. Since this type of sensor's basic design allows it to be provided in a wide range of geometries, automatic monitoring of critical process variables has in the past been made possible by simply selecting a combination of bob size and bob-channel dimensions that best matches the subject fluid's typical viscosity. I have now recognized, though, that a given individual sensor's range can be extended as a practical matter by making a subtle but significant change in the measurement technique.

Specifically, the approach I have devised bases the velocity determination (or computation of other velocity-related quantities) on position values inferred from the detection coil's output at predetermined times. As will be explained below, one of this approach's advantages is that it can be employed in such a fashion as to discriminate between data taken in portions of the path from which viscosity can be inferred with relative accuracy and data taken in portions from which velocity inferences would tend to be less accurate. As will also be explained in more detail below, using this approach to take multiple position measurements within a single traversal of the bob path can enable the sensor's range to be extended even without discriminating between the bob path's high-accuracy and low-accuracy measurements' positions.

DETAILED DESCRIPTION OF AN ILLUSTRATIVE EMBODIMENT

Figure 1:
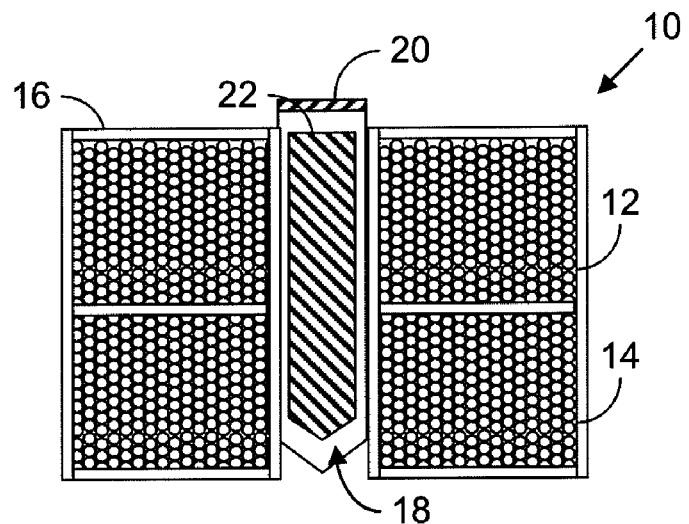
FIG. 1 is a simplified cross-sectional view of one type of reciprocating-bob sensor's coil-and-bob assembly.

FIG. 1 is cross-sectional view of one type of sensor that can employ the present invention's teachings. The sensor 10 is largely cylindrical and includes two separately driven coils 12 and 14 displaced axially from each other and isolated by a housing 16 from the liquid whose viscosity or other property is to be measured. But fluid is allowed to flow into a central sample well 18 at whose mouth is located a bob-retention spider 20, which confines a ferromagnetic bob 22 to the well 18. Alternately driving the two coils 12 and 14 causes the bob 22 to reciprocate against the sample liquid's viscous drag.

Figure 2:
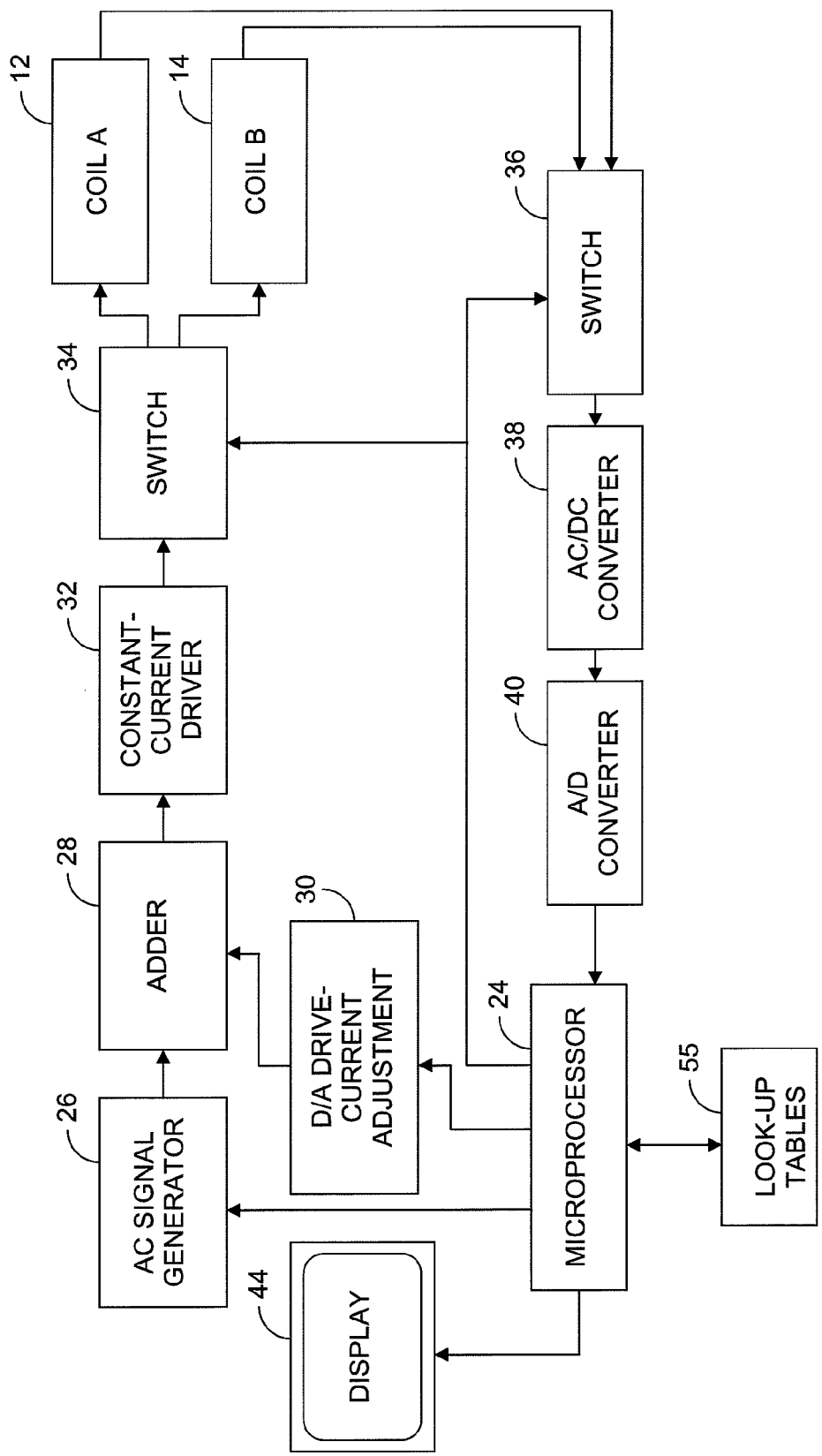
FIG. 2 is a block diagram of the sensor's circuitry.

FIG. 2 depicts control circuitry for achieving that result. A microprocessor 24 controls an AC-signal generator 26 to cause it to produce an AC signal that an adder circuit 28 adds to a DC signal from a microprocessor-controlled digital-to-analog converter 30. The resultant adder-28 output is a low-level AC voltage superimposed on a DC voltage whose level the microprocessor dictates. Filter 28 applies its output to a high-output-impedance current driver 32, i.e., a driver whose output current is determined by the driver's input largely independently of the load through which that current is driven. A switch 34 controlled by the microprocessor determines whether the current from driver 32 is applied to coil 12 or coil 14.

Microprocessor 24 operates a second switch 36 complementarily to switch 34: when switch 34 applies the current to coil 12, switch 36 applies to an AC-to-DC converter 38 a signal that mutual inductance between coils 12 and 14 causes in coil 14 in response to the drive current's AC component. An analog-to-digital converter 40 applies to the microprocessor 24 a digital representation of AC-to-DC converter 38's output, which is a DC voltage proportional to the amplitude of the switch-36-forwarded AC signal.

The analog-to-digital converter 40 applies those digital amplitude values to the microprocessor 24 periodically, multiple times during a single bob stroke. When the bob has reached a predetermined point in that stroke, the microprocessor changes the states of the switches 34 and 36 so that coil 14 is the one that is driven and coil 12 is the one whose voltage is sensed.

One type of measurement that such a circuit can be used to make is a simple fluid-characterization measurement. This measurement's purpose is to discriminate between Newtonian fluids and non-Newtonian fluids as well as between non-Newtonian fluids that are pseudoplastic and those that are dilatent.

It will be recalled that absolute (dynamic) viscosity is given by:

$$\eta = \frac{\sigma}{r_s}, \quad (1)$$

where $\eta$ is viscosity, $\sigma$ is shear stress (shear force per unit area), and $r_s$ is shear rate (velocity change per unit distance perpendicular to the shear direction).

A fluid is Newtonian if that viscosity is independent of the shear rate, it is pseudoplastic ("shear-thinning") if viscosity decreases with increasing shear rate, and it is dilatent ("shear-thickening") if its viscosity increases with increasing shear rate.

Figure 3A:
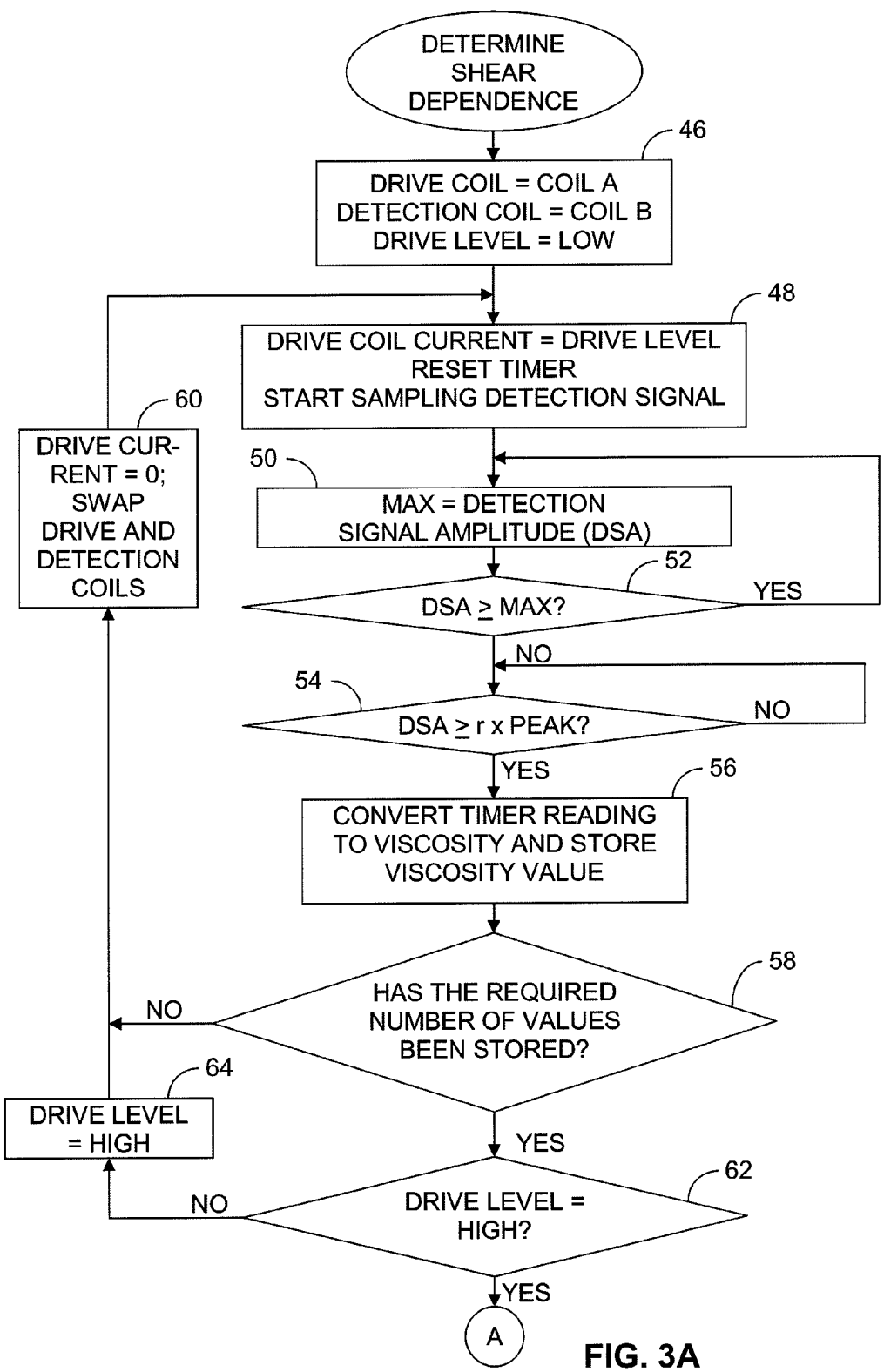
FIGS. 3A and 3B (together, "FIG. 3") form a flow chart of a routine that the sensor uses to determine a fluid's shear dependence.
Figure 3B:
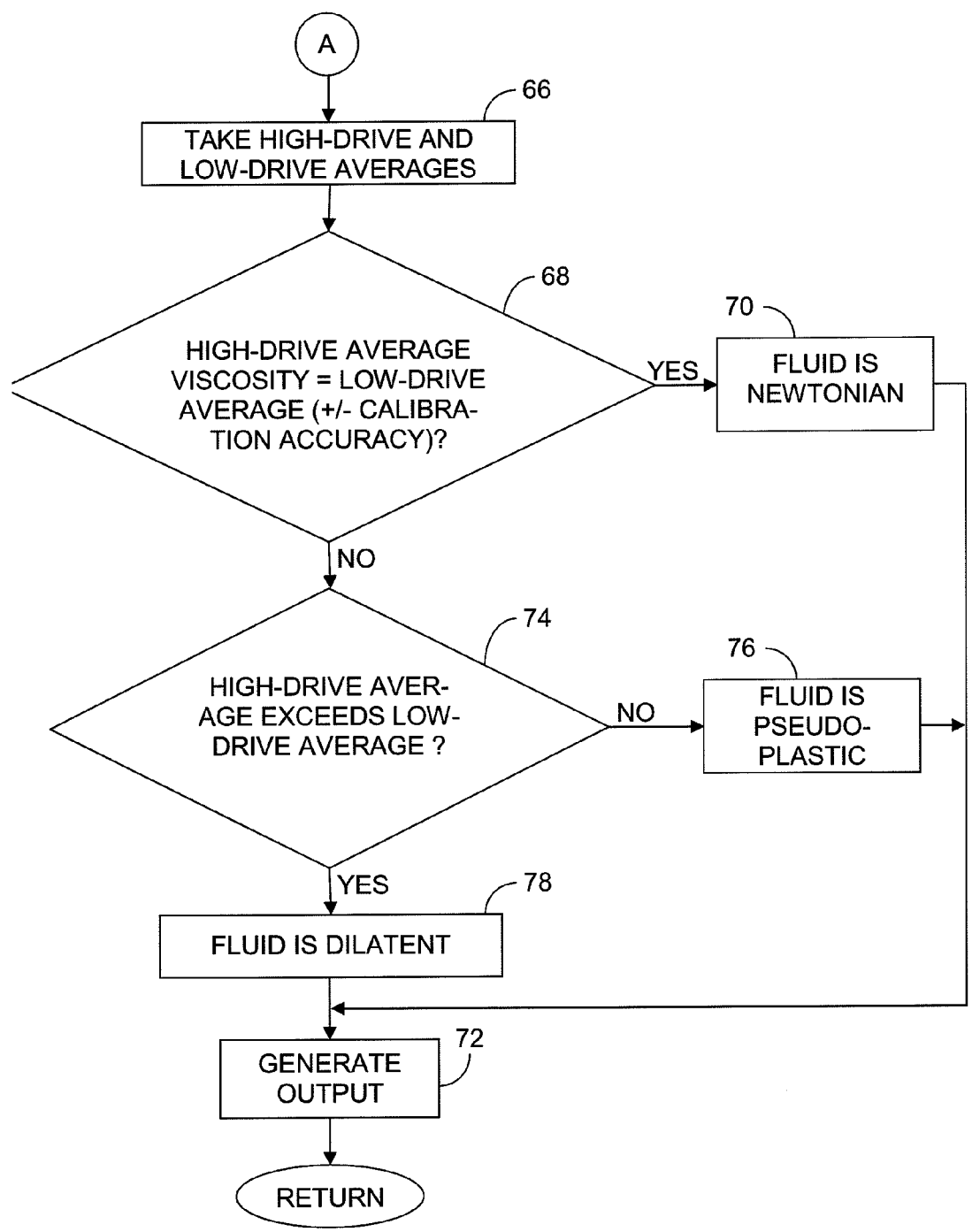

The illustrated system employs the FIG. 3 routine to discriminate among the three fluid types. As that drawing's block 46 indicates, the system is initialized before the first stroke by choosing one of the coils as the drive coil, choosing the other as the detection coil, and adopting as the initial drive-current level the lower of two levels that will be used in characterizing the sample fluid.

As block 48 indicates, the system then begins driving current through the drive coil at the selected drive level. As that block also indicates, the system starts the timer that will be used in determining relative viscosity, and it starts taking samples of the detection coil's signal amplitude.

Figure 4:
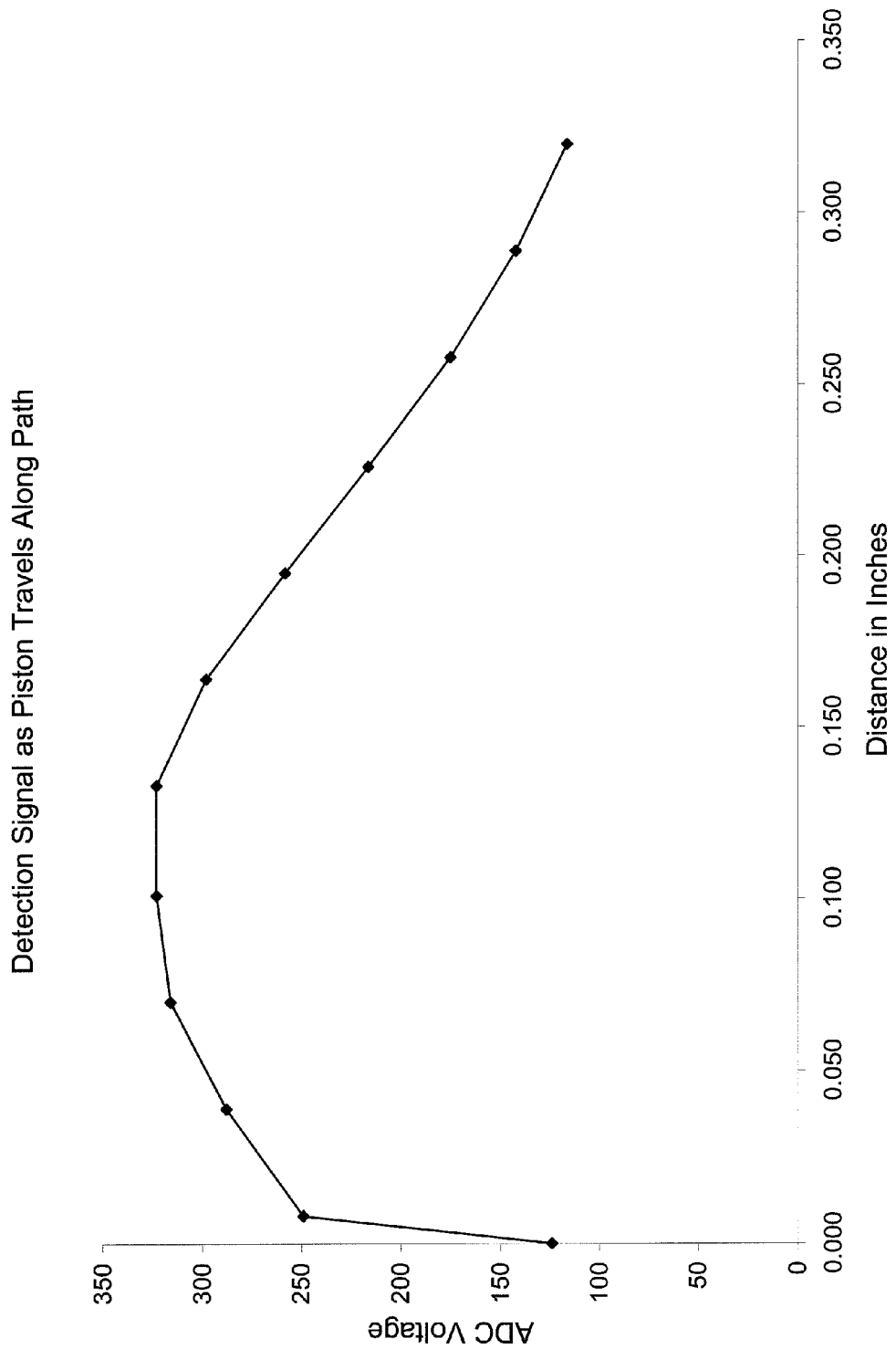
FIG. 4 is a plot of the sensor's sensor-coil output as a function of bob travel.

Bob-position changes that result from the magnetic force that the coil current causes tend to change the mutual inductance between the coils, with the result that the detection-coil amplitude is a function of bob position. FIG. 4 gives an example of such a function. As that drawing shows, the amplitude initially increases as the bob travel begins. Eventually, though, it reaches a peak, which the loop represented by FIG. 3's blocks 50 and 52 detects. As block 54 indicates, the routine then proceeds to identify an end point in the bob travel by determining when the detection-signal amplitude has fallen below a predetermined fraction of the peak thus detected.

When the system thereby concludes that the bob has reached its end point, the system reads the timer to determine how long the bob took to reach that point, and it infers the fluid's viscosity from that timer value. In the illustrated embodiment, it draws that inference by using the combination of drive level and travel time to address a look-up table (stored, for example, in a data-storage device represented by FIG. 2's block 55) that contains corresponding viscosity values. These values will typically have been obtained by calibrating the system with various fluids of known viscosities. Some embodiments may interpolate between stored values to increase resolution. Other embodiments may dispense with the look-up table entirely; the calibration may instead have been used to arrive the parameters of, say, best-fit polynomial approximations to the observed calibration data, in which case the resultant polynomial determined for the chosen drive level would be used to calculate the viscosity from the travel time. (Of course, some embodiments may use formulas that are not polynomials and/or that are functions of two or more variables—e.g., drive level and travel time—rather than just one.)

Now, the FIG. 3 embodiment's overall purpose is to take viscosity measurements at two different levels of drive current and therefore shear rate and to compare the results to determine whether the fluid is Newtonian. Instead of simply taking as the low-shear-rate viscosity value the result of the block-56 operation's first occurrence, the illustrated embodiment takes several such measurements. As block 58 indicates, that is, it determines whether it has taken enough low-shear-rate measurements. If it has not, it takes another measurement. To that end, it switches coils: as block 60 indicates, it adopts the erstwhile detection coil as the new drive coil and the erstwhile drive coil as the new detection coil. As that block also indicates, the system would typically turn off the drive current before making the switch. The measurement operation is then repeated with the bob traveling in the other direction, and such switching continues until enough low-shear-rate viscosity measurements have been made.

As blocks 62 and 64 indicate, the system then adopts a high-shear-rate current as the level with which to drive the coil, and several measurements are taken at the high shear rate.

As block 66 indicates, the system then takes respective averages of the high- and low-shear-rate measurements, which it compares. As blocks 68, 70, and 72 indicate, the system concludes that the fluid is Newtonian—and generates an output indicative of that conclusion on, e.g., FIG. 2's display 44—if the two averages differ by less than a predetermined tolerance value. As blocks 74, 76, and 78 indicate, on the other hand, the output displayed by the system indicates that the fluid is pseudoplastic if the high-shear-rate average is less than the low-shear-rate average by more than the tolerance, and it indicates that the fluid is dilatent if the high-shear-rate average exceeds the low-shear-rate average by more than that tolerance.

There are a number of applications in which it is desirable to know not only whether the fluid is Newtonian, pseudoplastic, or dilatent but also the degree to which a pseudoplastic or dilatent fluid exhibits that characteristic. There are a number of figures of merit conventionally employed to express the degree to which a fluid exhibits such a characteristic, and FIG. 5 is a flow chart of a routine for employing one of them. This particular routine is based on the observation that many fluids' behaviors are well approximated by the following power-law relationship between viscosity and shear rate in their highest-viscosity-variation regimes:

$$\eta = K\dot{\gamma}^{n-1}, \quad (2)$$

where 0 is viscosity, K is a constant coefficient, $\dot{\gamma}$ is the shear rate, and n is the so-called sensitivity factor. If the sensitivity factor n is unity, the fluid is Newtonian. If 0<n<1, the fluid is shear-thinning, i.e., pseudoplastic. If n>1, the fluid is shear-thickening, i.e., dilatent.

The FIG. 5 routine's operations 84-98 will be recognized as essentially the same as corresponding operations in the FIG. 3 routine with the exception that, instead of being chosen from only two values, the coil-current level adopted in step 84 is chosen from a larger number, and an average viscosity value is determined for each of that larger number of drive—and therefore shear-rate—levels. As blocks 100, 102, 104 and 106 indicate, the system steps through measurements at those levels and then turns the coil current off.

Block 108 represents determining the shear sensitivity from the resultant observed relationship between average viscosity and shear rate by finding the value of n that yields the best fit of the above-stated power-law relationship to the measured average-viscosity values. In doing so, it uses the relationship between shear rate and elapsed time that the sensor's geometry dictates. As block 110 indicates, the system generates an appropriate output to represent that calculation's result.

As was stated above, the power-law relationship tends to apply to only the fluid's highest-viscosity-variation regime, so the operation represented by block 108 may include identifying that regime by comparing the viscosity values that result from successive drive levels. The curve-fitting operation would then be applied to that regime. Other embodiments may instead identify that regime by preceding the block-84 operation with initial viscosity measurements taken at widely spaced drive levels, in which case the drive levels chosen in the block-104 operation can be restricted to those in the power-law regime.

In any event, the output generated in the block-110 operation can take any of a wide variety of forms. For example, it may simply be the numerical value of the shear sensitivity n itself. It could be that value together with an indication, in terms of, say, the shear-rate range, of the regime in which the determined power-law relationship prevails. Yet another type of output may be a plot of viscosity as a function of shear rate, possibly in addition to one or both of the numerical values mentioned above.

Figure 6:
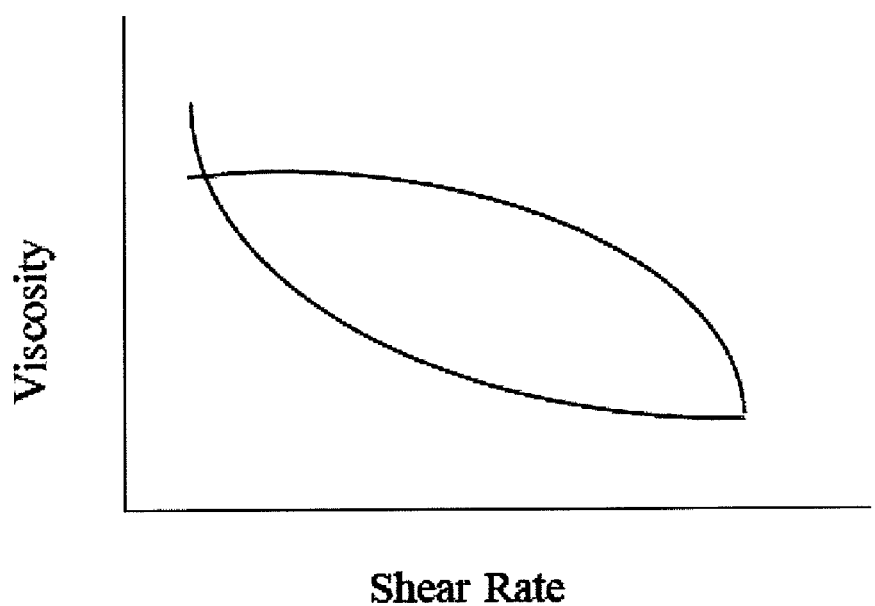
FIG. 6 is a graph containing viscosity-vs.-shear-rate plots that result from different shear-rate sequences applied to a fluid that exhibits shear memory.

Particularly in the latter connection it is sometimes instructive to take into account the fact that some fluids exhibit a shear-rate "memory": the viscosities that they exhibit can depend on the shear rates that they have recently experienced. One way to take this into account is to perform the FIG. 5 operation twice, once in increasing-drive-level order and once in decreasing-drive-level order, and to produce an output plot that shows the resultant "hysteresis," which FIG. 6 illustrates.

Figure 7:
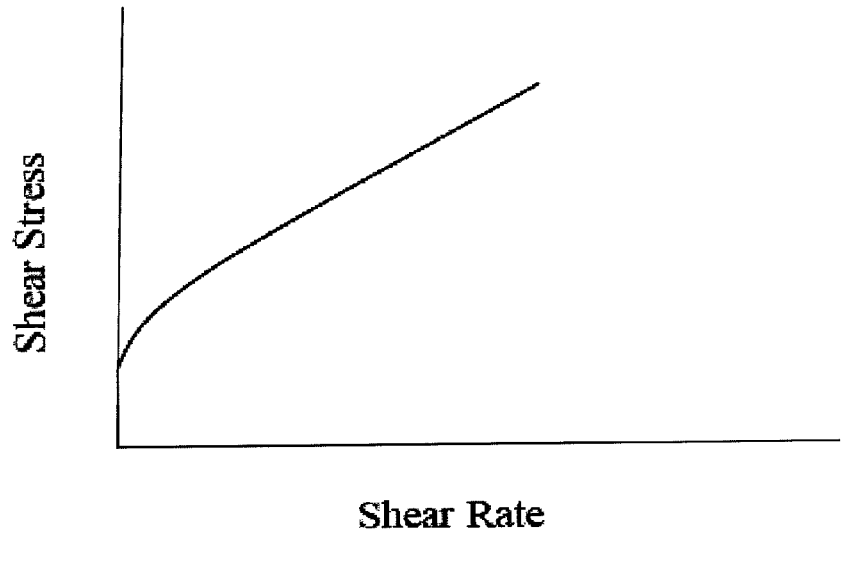
FIG. 7 is a typical plot of shear stress as a function of shear rate.

By a slight change, the approach described by reference to FIG. 5 for determining shear sensitivity can also be used to provide an output indicative of shear stress as a function of shear rate to produce, say, a graphical output such as that which FIG. 7 depicts. Specifically, the operation of FIG. 5B's block 108 can be replaced with one in which shear stresses are computed for respective rates from that routine's previous measurements.

Figure 5A:
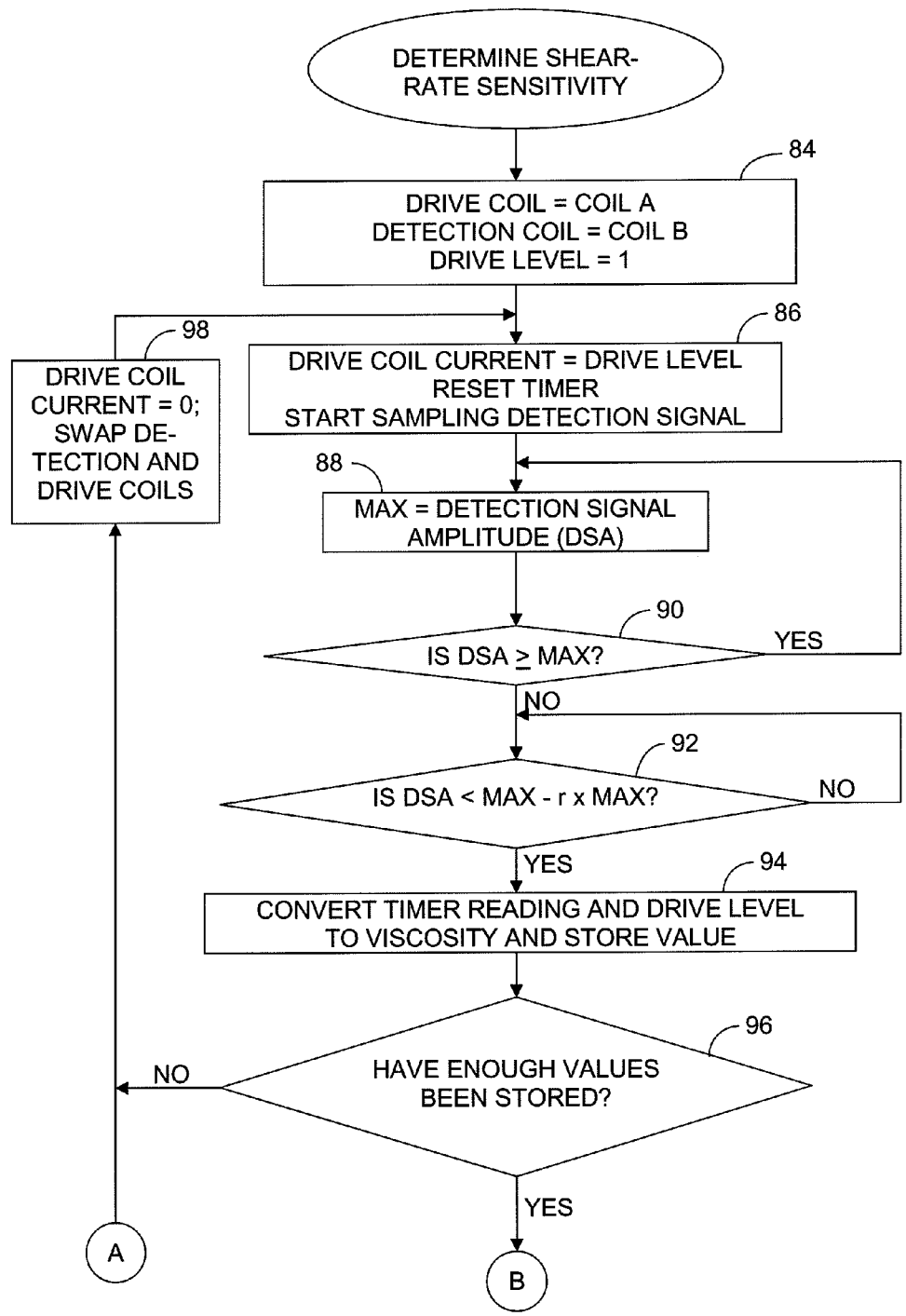
FIGS. 5A and 5B (together, "FIG. 5") form a flow chart of a routine that the sensor uses to determine shear-rate sensitivity.
Figure 5B:
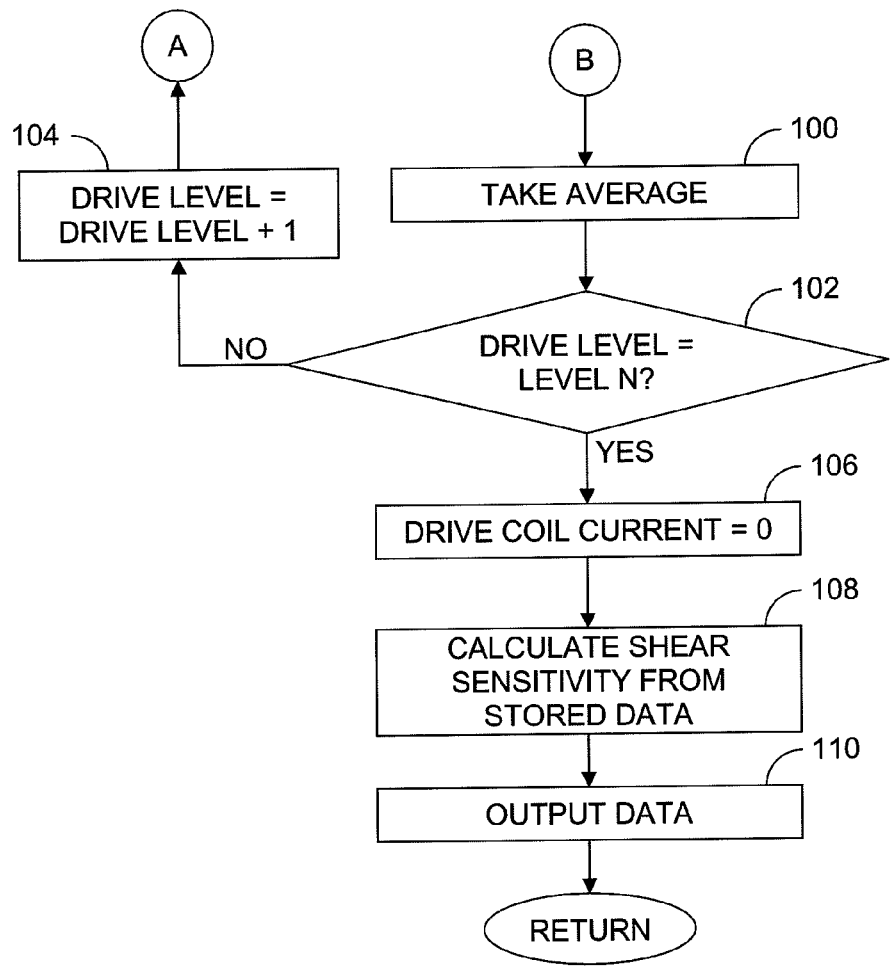

Since known-viscosity fluids were used to arrive at the illustrated embodiment's look-up-table or algorithmic relationship between viscosity and the combination of drive level and travel time, those known relationships can be used to obtain viscosity in FIG. 5A's block-94 operation as an intermediate value, and the shear stress can be calculated as the product of shear rate and the thus-determined viscosity. Of course, some embodiments may instead obtain shear stress more directly, without the intermediate viscosity computation; the relationship between shear stress and coil current can be obtained from the sensor geometry and relationships (typically determined during a calibration operation) between coil current and resultant magnetic force on the bob.

Figure 8:
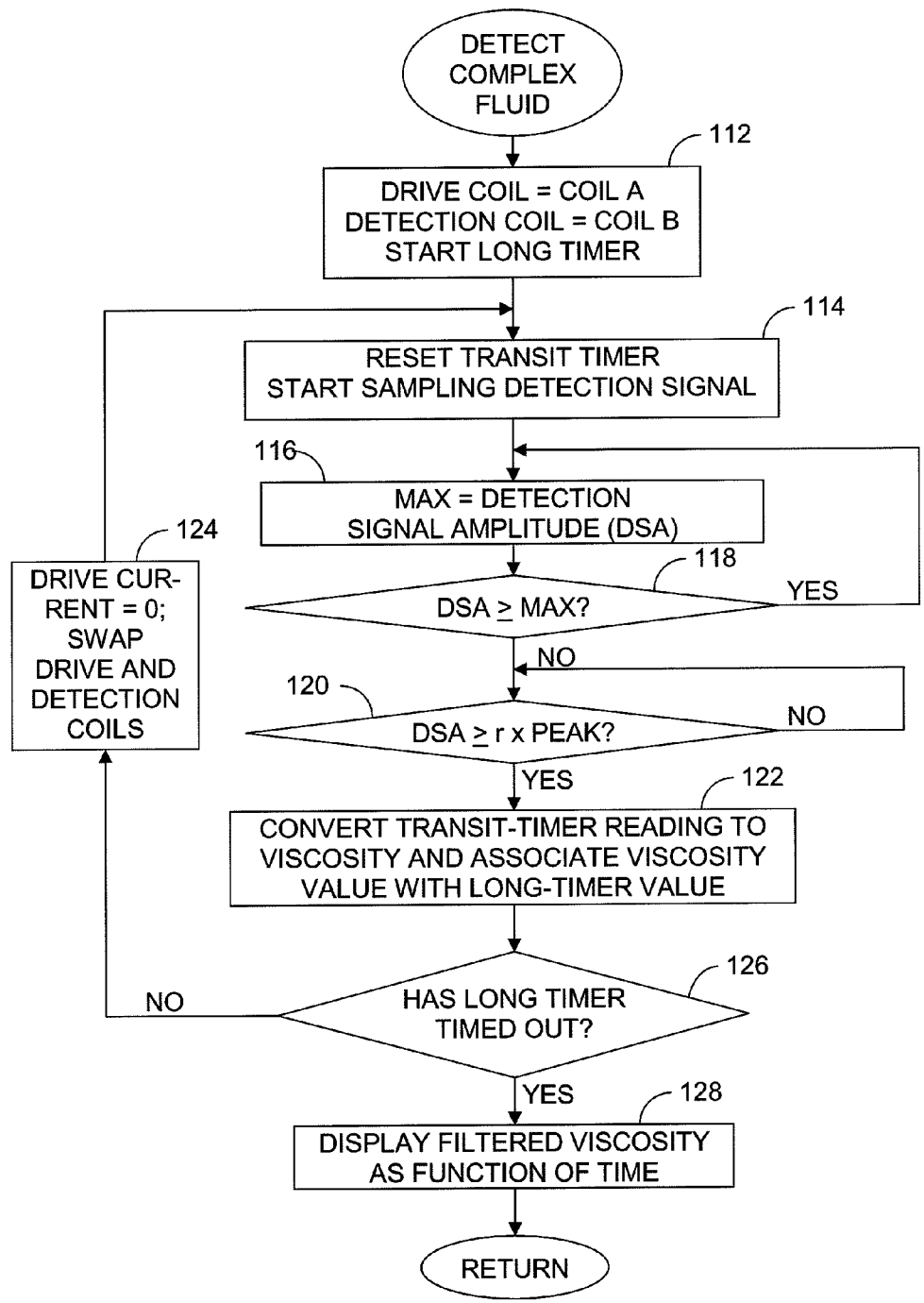
FIG. 8 is a flow chart of a routine that the sensor uses to detect fluid complexity.

Another type of measurement that reciprocating-bob sensors can be used for is the detection of fluid complexity, i.e., of the tendency of a fluid's viscosity to change with time when it is being sheared. FIG. 8 depicts an approach that can be used for that purpose. This measurement would likely be made over a relatively extended time period; a duration of half an hour may be used, for instance. As block 112, indicates, therefore, the operation's initialization includes setting a "long timer" intended for such durations. The operations that blocks 114, 116, 118, 120, 122, and 124 represent will be familiar from previous routines as the operations by which the system causes the bob to reciprocate and make viscosity determinations based on its motion. Block 126 indicates that this reciprocation and viscosity measurement continue until the long timer has timed out. Typically, this measurement is made with the same drive-current level on each stroke.

As block 128 indicates, the system then generates an output that tells whether shearing has caused drift in the fluid's viscosity. In the illustrated embodiment, that is done by presenting as a graphical output a plot of filtered viscosity values as a function of time. The filter is used for noise suppression and may, for instance, produce the viscosity's exponential average. Other embodiments may instead or additionally state whether the fluid is complex or not, basing that determination on whether a detected change exceeds some threshold, and, if it is complex, whether it is rheopectic (thickening over time) or thixotropic (thinning over time).

Figure 9A:
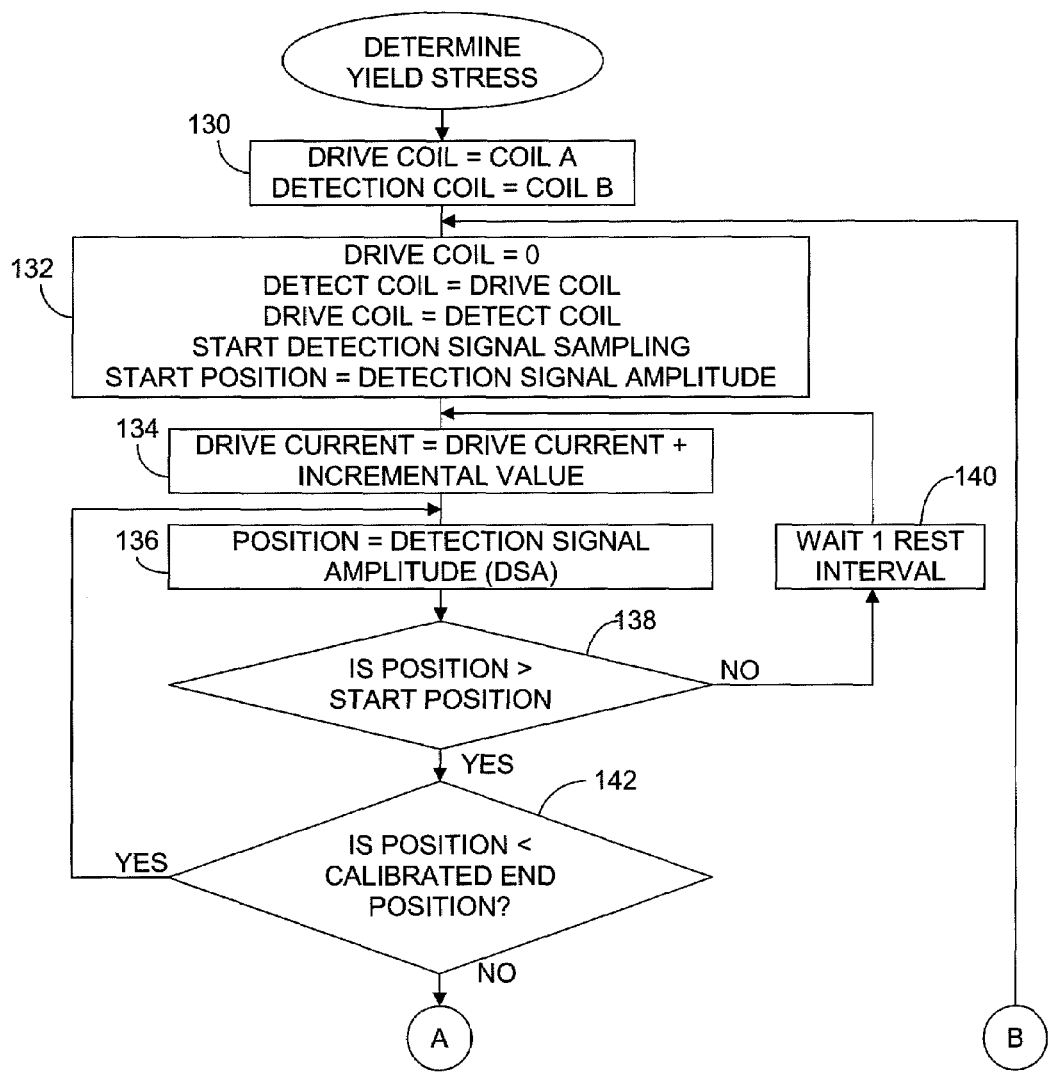
FIGS. 9A and 9B (together, "FIG. 9") are a flow chart of a routine that the sensor uses to determine a fluid's yield stress.
Figure 9B:
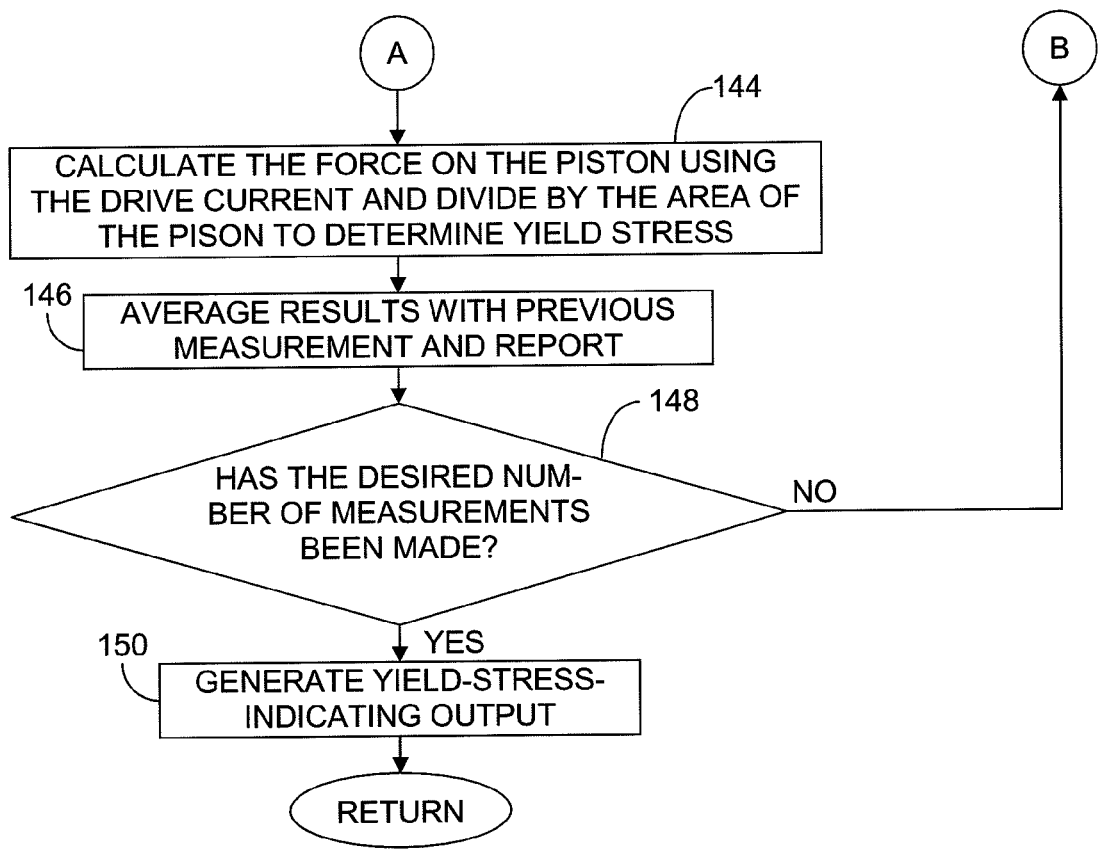

The reciprocating-bob sensor can also be used to determine yield stress. Some fluids do not flow until they are subjected to a threshold stress, and FIG. 9 depicts one routine for determining that threshold. Block 130 represents initialization for the routine as a whole, while block 132 represents initialization for a single stroke. As block 132 indicates, the drive current is initially zero, and, as blocks 134, 136, 138, and 140 indicate, it increases incrementally with a rest interval between increases until the detection coil's signal indicates that the bob has moved from the initial position. Once that motion has been detected, the system keeps driving the bob in the same direction (with, in the illustrated embodiment, the same drive current) until it reaches the end-of-stroke position as determined in an operation that block 142 represents. As blocks 144, 146, and 148 indicate, the system repeats this operation, inferring yield stress from the current that was applied when initial movement was detected and averaging the result with previous measurements, until some predetermined number of such measurements have been made. As block 150 indicates, the routine then generates an output indicating the average yield-stress value, although, as block 146 indicates, it may also output intermediate values, too.

The above-described routines that determine viscosity do so by timing the bob's travel through a predetermined distance. In this respect, their uses of the sensor are similar to those that conventional approaches employ. In contrast, the routine of FIG. 10 determines viscosity by measuring the distances traveled by the bob in predetermined time increments: the measured quantity is distance rather than time. The particular approach that FIG. 10 employs tends extend the range of viscosities that a given sensor can be employed to measure. It does this by making incremental velocity measurements: it makes multiple measurements in the span of the single bob stroke or less. That routine can be used simply to make a viscosity measurement or it can be employed as a constituent of a more-elaborate rheological measurement. It can, for example, be substituted for the operations of FIG. 3's blocks 50, 52, 54, and 56, FIG. 5's blocks 88, 90, 92, and 94, and FIG. 8's blocks 116, 118, 120, and 122.

Figure 10A:
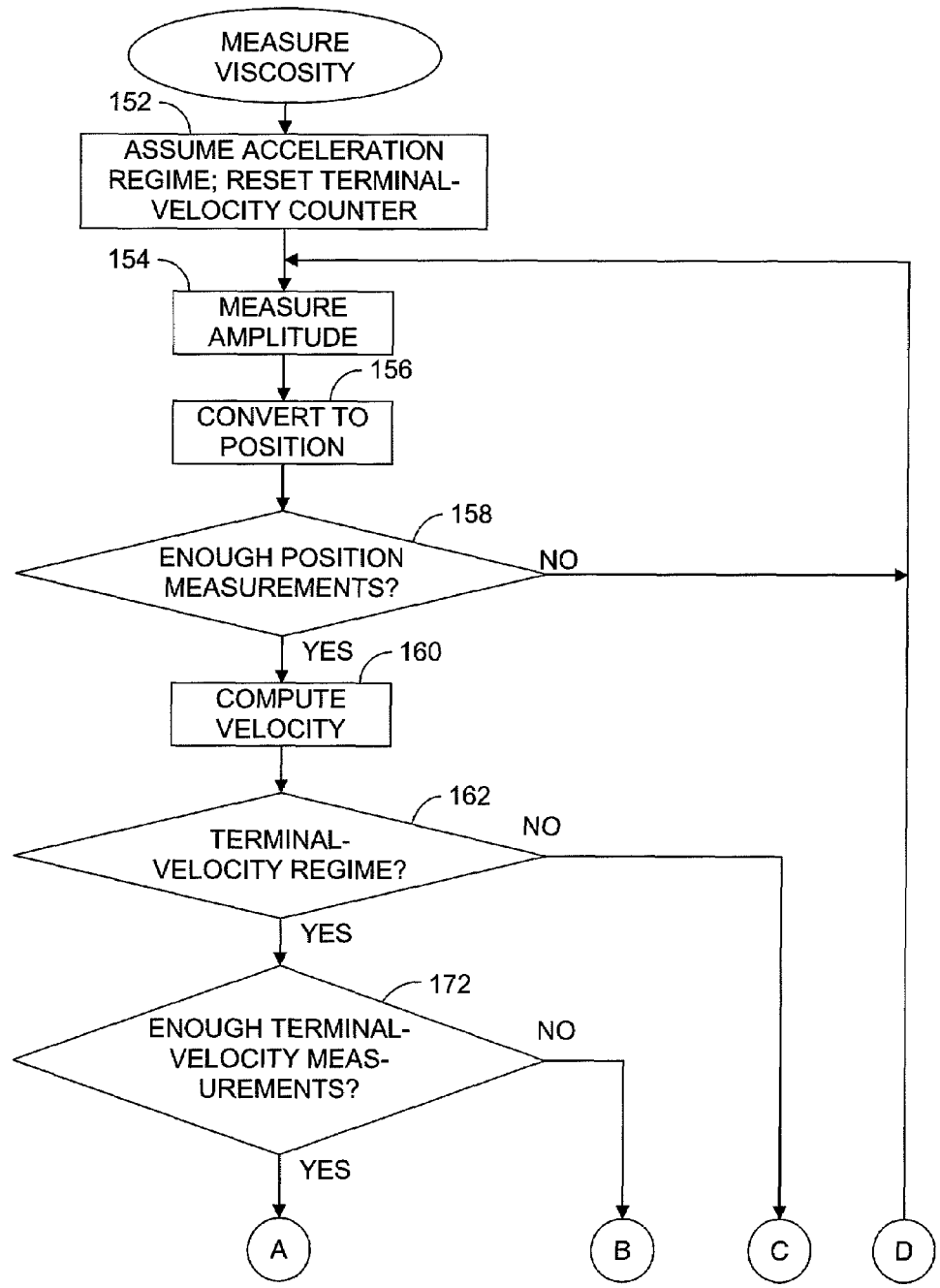
FIGS. 10A and 10B (together, "FIG. 10") form a flow chart of a routine that the sensor uses to measure viscosity.
Figure 10B:
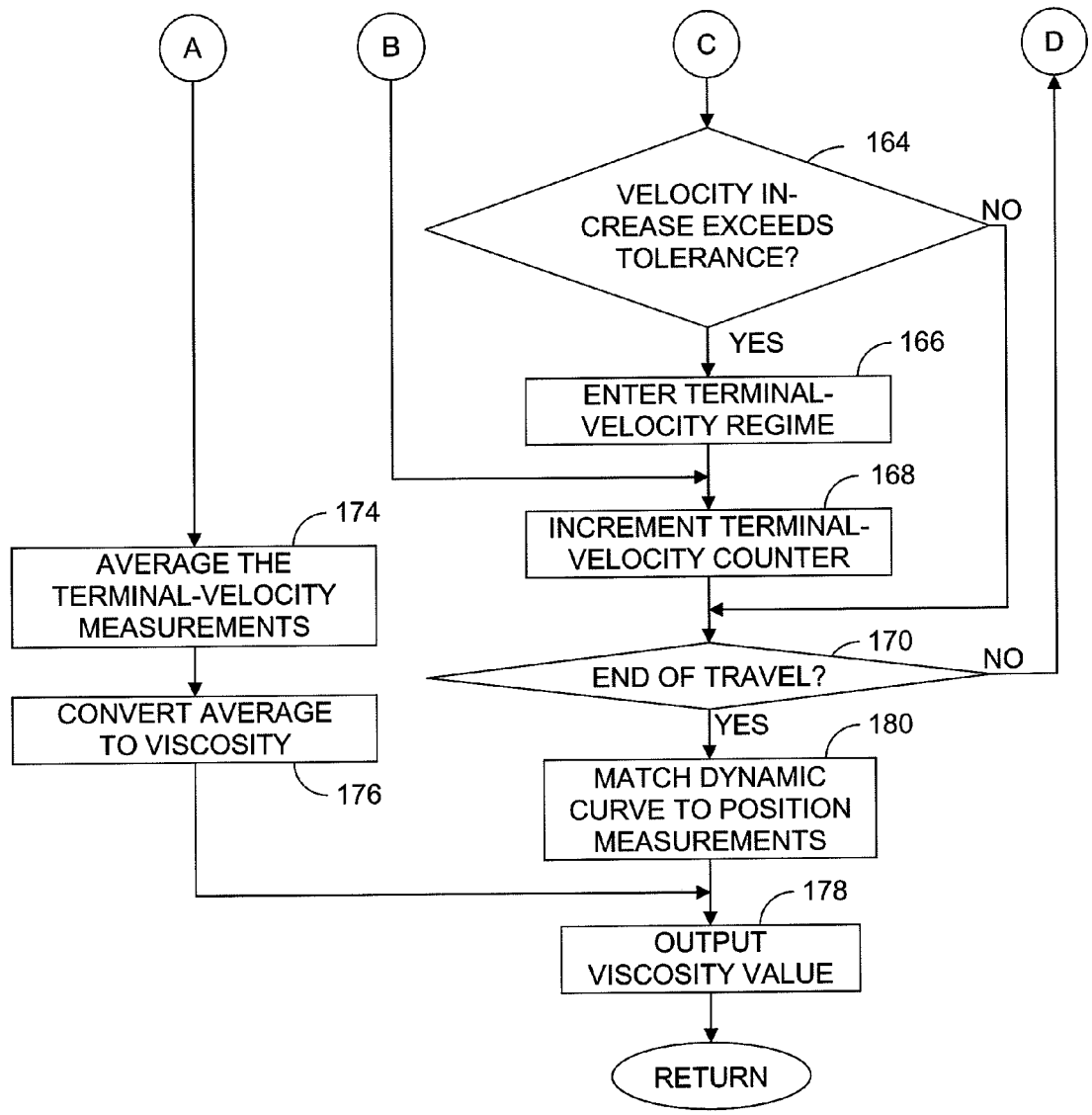

For purposes that will become apparent, the FIG. 10 routine begins in an initialization operation that block 152 represents. That initialization operation includes setting a flag to a state that indicates that the bob motion is currently in an acceleration regime rather than a terminal-velocity regime. Additionally, the system resets a terminal-velocity-measurement counter to zero, as block 152 indicates. As will be described in more detail below, that counter indicates how many individual velocity measurements have been made in the terminal-velocity regime.

With that flag and counter set, the system begins driving the bob electromagnetically in the manner explained above. Periodically during the resultant bob stroke it measures the amplitude of the detection coil's output signal, as block 154 indicates. By employing one of the approaches mentioned above the system then converts the amplitude measurement to a position value, as block 156 indicates.

These position measurements will be used to compute velocity at various points along the stroke. Of course, a velocity determination can be made from only two position measurements, and some embodiments may employ only two position measurements for each velocity calculation. For noise-suppression purposes, though, other embodiments may employ three or more position measurements and use some type of filtering approach to arrive at a velocity value.

Since a velocity calculation requires multiple position measurements, not enough position values will be available initially. As block 158 indicates, therefore, the system computes no velocity values until enough position values have been taken. After they have, the system computes a velocity for each subsequent position value, as block 160 indicates, by using as position-measurement window that overlaps the window used for the previous velocity computation. If the fluid is relatively inviscid, the bob may travel through a significant portion of its stroke before it reaches its terminal velocity. The velocities observed in this initial, pre-terminal-velocity portion of its stroke result partially from inertial effects, so the accuracy of viscosity determinations made in that regime can suffer if appropriate provisions are not made to take those inertial effects into account.

The routine that FIG. 10 depicts employs two alternative approaches to making such provisions. The first is simply to avoid velocity measurements in that initial portion of the stroke. As was mentioned above, the system assumes at the beginning of the stroke that the bob is in an acceleration phase, where inertia significantly affects bob velocity. In a manner that will described below, the system therefore tests the position measurements to determine whether it should assume that the bob has reached the terminal-velocity portion of its travel. Block 162 represents checking the flag that indicates whether the system has already concluded that this regime has been reached. If the terminal-velocity regime has not yet been assumed, i.e., if the flag indicates that the system has not yet concluded that the bob has reached its terminal velocity, the sensor determines whether such a conclusion would now be justified. As block 164 indicates, it does this by determining whether the just-computed velocity exceeds the previously determined velocity by more than some predetermined increment. If not, the system switches the flag, as block 166 indicates, to the terminal-velocity-regime-indicating value Once the bob has entered the terminal-velocity regime, some number of velocity determinations thereafter made will be the basis for a viscosity computation. To keep track of whether the requisite number of terminal-velocity measurements have been made, the system uses a counter, which block 168 represents incrementing. As block 170 indicates, the system then returns to make another of the terminal-velocity-regime measurements if the bob has not reached the end of its travel.

The end-of-travel determination can be made in the above-mentioned manner, in which it is based on whether the detection-coil output has fallen to a predetermined fraction of its peak value. But another approach, which for some sensor arrangements is more accurate, is to observe whether the bob has reached a hard stop, i.e., to determine whether two successive position measurements are equal or nearly so.

In any event, the block-170 operation's conclusion will ordinarily be that the bob has not reached the end of its travel, so the system returns to make a further terminal-velocity-regime measurement. This time, the determination represented by FIG. 5's block 162 is affirmative, representing the system's conclusion that the terminal-velocity regime has been reached, so the system does not return to the block-164 determination. Instead, it performs the operation represented block 172, in which it reads the terminal-velocity counter to determine whether enough terminal-velocity measurements have been made to provide a good basis for a viscosity computation. If not enough have, that velocity measurement is simply stored, and the system repeats the block-168 and -170 operations of incrementing the terminal-velocity counter and making the end-of-travel determination. This loop continues in most cases until the block-172 determination is affirmative, i.e., until enough terminal-velocity-regime measurements have been made. When enough have, the routine performs the block-174 operation of averaging the velocity measurements that were made in the terminal-velocity regime; the average is based only on those measurements and not on any of the velocities that were observed during the initial, acceleration regime.

In some embodiments, the criterion applied by the block-172 determination may not be a fixed number of terminal-velocity-regime velocity measurements; the system may, for example, merely continue to take terminal-velocity-regime velocity measurements until the bob reaches the end of its stroke, and all of the measurements thus taken contribute to the average. In other embodiments, though, the criterion may be a predetermined number so that a first viscosity (or other velocity-related-quantity) computation can be completed before a full stroke ends. The rest of the stroke can then be used for another computation of viscosity (or, e.g., shear rate), possibly based on a different drive current.

As block 176 indicates, the system infers viscosity (or some other velocity-related quantity) from the average velocity value in one of the ways mentioned above. The routine ends after the block-178 operation of generating an appropriate output indicative of that value. In some cases that output will simply be a presentation on a human-readable display. In other cases it may, for instance, be provided as one constituent input to some fluid-characteristic determination based on some number of such values or on one or more such values together with values of one or more other physical quantities.

As was mentioned above, the routine actually provides for two alternative approaches to determining viscosity. The first one, just described, is the one that is employed in situations in which the terminal-velocity regime's duration is long enough to provide enough terminal-velocity-regime measurements for a determination of viscosity or other desired quantity. In some cases, though, the viscosity is so low that too few velocity measurements have been taken in the terminal-velocity regime. In such cases, there will eventually be an affirmative outcome of the block-170 determination: the bob will reach the end of its travel before enough terminal-velocity-regime measurements been made.

In that situation, the system employs an alternative approach, in which it infers velocity by mathematically matching dynamic motion curves to the position measurements that were taken during the stroke. For example, the system may have previously determined that the sample fluid is Newtonian. In that case, it may be assumed that the equation of motion will be of the form:

$$m\frac{d^2 y}{dt^2} + k_g \eta \frac{dy}{dt} = F, \quad (3)$$

where m is the bob's mass, y is its position, $k_g$ is a geometry-determined coefficient that relates the viscous drag on the bob to the fluid's viscosity $\eta$ and the bob's speed, and F is the (in the illustrated embodiment, substantially constant) magnetic force on the bob. That differential equation's solution for boundary value y=dy/dt=0 at t=0 is $$y(t) = [t - (1 - e^{-t/\tau})\tau] v_T, \quad (4)$$

where $v_T = F/k_g \eta$ is the bob's terminal velocity and $\tau = m/k_g \eta$ is the time constant with which the bob's velocity approaches $v_T$.

Since the force F and coefficient $k_g$ will be known, the fluid's viscosity can be computed from the bob motion's time constant $\tau$ or terminal velocity $v_T$. So all that is necessary is to use some curve-fitting routine to find the time constant that results in the best match of the observed position values to the above differential-equation solution. One approach, for example, is to begin by assuming a trial time constant equal to, say, the just-observed stroke time and to use this assumed time-constant value to compute a respective terminal-velocity value from each of a plurality of the observed (time, position) pairs in accordance with the following equation:

$$v_T = \frac{y(t)}{t - (1 - e^{-t/\tau})\tau} \quad (5)$$

If the assumed time constant is correct, each of the terminal-velocity values thus determined will be approximately the same. If the assumed time constant is too low, though, they will increase with time, and they will decrease with time if it is too high. By employing those facts, the system can arrive at the correct time constant, and therefore the correct viscosity value, by successive approximation.

By employing the present invention's teachings, a wide range of rheological measurements can be made inexpensively. The invention therefore constitutes a significant advance in the art.

What is claimed is:

1. A method of fluid characterization that includes:
   A) driving current through a first coil in such a manner as thereby to drive a ferromagnetic bob magnetically through a bob path occupied by a sample fluid and induce in a second coil by mutual inductance a resultant detection-coil signal that depends on the bob's position along the bob path;
   B) taking measurements of the detection-coil signal's values at a plurality of times during a single traversal of the bob path;
   C) determining respective bob positions from a plurality of the values of the detection-coil signal thus measured during that single traversal;
   D) determining a rheological characteristic of the sample fluid from a plurality of the bob positions thus determined by:
      i) computing a plurality of velocity values from the determined bob positions;
      ii) classifying sequences of the measurements taken in a single traversal into acceleration and terminal-velocity regimes in accordance with comparisons of successive said velocity values; and
      iii) basing determination of the rheological characteristic from the measurements taken in the terminal-velocity regime without employing the measurements taken in the acceleration regime; and
   E) generating a characterizer output signal indicative of the rheological characteristic thus determined.

2. A method as defined in claim 1 wherein determining the rheological characteristic includes computing the sample fluid's viscosity.

3. A method as defined in claim 1 wherein determining the rheological characteristic includes mitigating inertial effects.

4. A method as defined in claim 3 wherein determining the rheological characteristic includes computing the sample fluid's viscosity and mitigating inertial effects in doing so.

5. A method as defined in claim 1 wherein determining the rheological characteristic includes computing the sample fluid's viscosity from the measurements taken in the terminal-velocity regime without employing the measurements taken in the acceleration regime.

6. A method as defined in claim 1 wherein:
   A) the method additionally includes so driving current through the second coil as thereby to drive the ferromagnetic bob magnetically back through the bob path and induce in the first coil by mutual inductance a resultant detection-coil signal that depends on the bob's position along the bob path; and
   B) the bob positions are additionally determined from values of the detection signal measured at a plurality of times as the bob is driven back through the bob path.

7. A method as defined in claim 1 wherein the characterizer output signal indicates whether the sample fluid is Newtonian.

8. A method as defined in claim 7 wherein the characterizer output signal also indicates whether the fluid is a shear-thinning or shear-thickening fluid if the characterizer output signal indicates that the fluid is not Newtonian.

9. A method as defined in claim 1 wherein a characterizer output represents how sensitive the sample fluid's viscosity is to shear rate.

10. A method as defined in claim 1 wherein the characterizer output represents shear stress on the sample fluid as a function of the shearing that the sample fluid undergoes.

11. A method as defined in claim 1 wherein:
A) the driving of the ferromagnetic bob through the bob path occurs repeatedly throughout a measurement duration; and
B) the characterizer output signal represents the sample fluid's viscosity as a function of how long the bob has been driven repeatedly through the fluid.

12. A fluid characterizer comprising:
A) a ferromagnetic-bob-type instrument comprising:
   i) a sample well;
   ii) a ferromagnetic bob disposed in the sample well for reciprocation in first and second directions along a bob path therethrough; and
   iii) first and second coils so disposed with respect to the sample well that current driven through the first coil results in magnetic force that tends to drive the bob in the first direction, that current driven through the second coil results in magnetic force that tends to drive the bob in the second direction, and that mutual inductance between the coils depends on the bob's position;
B) control circuitry that includes:
   i) driver circuitry for so driving current including an AC component through at least the first coil as to drive the bob in at least the first direction through fluid contained by the sample well;
   ii) sensor circuitry for sensing a signal that the AC component driven through one of the coils causes in the other of the coils by mutual inductance and for generating a sensor output representative thereof, and
   iii) computation circuitry for generating from the sensor output a characterizer output that represents the fluid's yield stress.

13. A fluid characterizer comprising:
A) a ferromagnetic-bob-type instrument comprising:
   i) a sample well;
   ii) a ferromagnetic bob disposed in the sample well for reciprocation in first and second directions along a bob path therethrough; and
   iii) first and second coils so disposed with respect to the sample well that current driven through the first coil results in magnetic force that tends to drive the bob in the first direction, that current driven through the second coil results in magnetic force that tends to drive the bob in the second direction, and that mutual inductance between the coils depends on the bob's position;
B) control circuitry that includes:
   i) driver circuitry for so driving current including an AC component through at least the first coil as to drive the bob in at least the first direction through fluid contained by the sample well;
   ii) sensor circuitry for sensing a signal that the AC component driven through one of the coils causes in the other of the coils by mutual inductance and for generating a sensor output representative thereof, and
   iii) computation circuitry for generating from the sensor output a characterizer output that represents the shear stress on the fluid as a function of the shearing that the fluid undergoes.

14. A fluid characterizer comprising:
A) a ferromagnetic-bob-type instrument comprising:
   i) a sample well;
   ii) a ferromagnetic bob disposed in the sample well for reciprocation in first and second directions along a bob path therethrough; and
   iii) first and second coils so disposed with respect to the sample well that current driven through the first coil results in magnetic force that tends to drive the bob in the first direction, that current driven through the second coil results in magnetic force that tends to drive the bob in the second direction, and that mutual inductance between the coils depends on the bob's position;
B) control circuitry that includes:
   i) driver circuitry for so driving current including an AC component through at least the first coil as to drive the bob in at least the first direction through fluid contained by the sample well;
   ii) sensor circuitry for sensing a signal that the AC component driven through one of the coils causes in the other of the coils by mutual inductance and for generating a sensor output representative thereof, and
   iii) computation circuitry for generating from the sensor output a characterizer output that indicates how sensitive the fluid's viscosity is to shear rate.

15. A fluid characterizer comprising:
A) a ferromagnetic-bob-type instrument comprising:
   i) a sample well;
   ii) a ferromagnetic bob disposed in the sample well for reciprocation in first and second directions along a bob path therethrough; and
   iii) first and second coils so disposed with respect to the sample well that current driven through the first coil results in magnetic force that tends to drive the bob in the first direction, that current driven through the second coil results in magnetic force that tends to drive the bob in the second direction, and that mutual inductance between the coils depends on the bob's position; and
B) control circuitry that includes:
   i) driver circuitry for so driving current including an AC component through the first and second coils as to drive the bob in at least the first direction through a sample fluid contained by the sample well;
   ii) sensor circuitry for taking measurements of the values, at a plurality of times during a single traversal of the bob path, of a detection-coil signal that the AC component driven through one of the coils causes in the other of the coils by mutual inductance and for generating a sensor output representative thereof; and
   iii) computation circuitry for:
      a) determining respective bob positions from a plurality of the values of the detection-coil signal thus measured during that single traversal;
      b) determining a rheological characteristic of the sample fluid from a plurality of the bob positions thus determined by:
         1) computing a plurality of velocity values from the determined bob positions;
         2) classifying sequences of the measurements taken in a single traversal into acceleration and terminal-velocity regimes in accordance with comparisons of successive said velocity values; and
         3) basing determination of the rheological characteristic from the measurements taken in the terminal-velocity regime without employing the measurements taken in the acceleration regime; and c) generating a characterizer output signal indicative of the rheological characteristic thus determined.

16. A fluid characterizer as defined in claim 15 wherein determining the rheological characteristic includes computing the sample fluid's viscosity.

17. A fluid characterizer as defined in claim 15 wherein determining the rheological characteristic includes mitigating inertial effects.

18. A fluid characterizer as defined in claim 17 wherein determining the rheological characteristic includes computing the sample fluid's viscosity and mitigating inertial effects in doing so.

19. A fluid characterizer as defined in claim 15 wherein determining the rheological characteristic includes computing the sample fluid's viscosity from the measurements taken in the terminal-velocity regime without employing the measurements taken in the acceleration regime.

20. A fluid characterizer as defined in claim 15 wherein:
A) the driver circuit so drives current through the second coil as thereby to drive the ferromagnetic bob magnetically back through the bob path and induce in the first coil by mutual inductance a resultant detection-coil signal that depends on the bob's position along the bob path; and
B) the computation circuit additionally determines the bob positions from values of the detection signal measured at a plurality of times as the bob is driven back through the bob path.

21. A fluid characterizer as defined in claim 15 wherein the characterizer output signal indicates whether the sample fluid is Newtonian.

22. A fluid characterizer as defined in claim 21 wherein the characterizer output signal also indicates whether the fluid is a shear-thinning or shear-thickening fluid if the characterizer output signal indicates that the fluid is not Newtonian.

23. A fluid characterizer as defined in claim 15 wherein a characterizer output represents how sensitive the sample fluid's viscosity is to shear rate.

24. A fluid characterizer as defined in claim 15 wherein the characterizer output represents shear stress on the sample fluid as a function of the shearing that the sample fluid undergoes.

25. A fluid characterizer as defined in claim 15 wherein:
A) the driving of the ferromagnetic bob through the bob path occurs repeatedly throughout a measurement duration; and
B) the characterizer output signal represents the sample fluid's viscosity as a function of how long the bob has been driven repeatedly through the fluid.

26. A method of fluid characterization that includes:
A) providing a ferromagnetic-bob-type instrument that includes:
i) a sample well;
ii) a ferromagnetic bob disposed in the sample well for reciprocation in first and second directions along a bob path therethrough; and
iii) first and second coils so disposed with respect to the sample well that current driven through the first coil results in magnetic force that tends to drive the bob in the first direction, that current driven through the second coil results in magnetic force that tends to drive the bob in the second direction, and that mutual inductance between the coils depends on the bob's position;
B) so driving current including an AC component through at least the first coil as to drive the bob in at least the first direction through fluid contained by the sample well;
C) sensing a signal that the AC component driven through one of the coils causes in the other of the coils by mutual inductance;
D) generating a sensor output representative thereof, and
E) generating from the sensor output a characterizer output that indicates at least the fluid's yield stress.

27. A method of fluid characterization that includes:
A) providing a ferromagnetic-bob-type instrument that includes:
i) a sample well;
ii) a ferromagnetic bob disposed in the sample well for reciprocation in first and second directions along a bob path therethrough; and
iii) first and second coils so disposed with respect to the sample well that current driven through the first coil results in magnetic force that tends to drive the bob in the first direction, that current driven through the second coil results in magnetic force that tends to drive the bob in the second direction, and that mutual inductance between the coils depends on the bob's position;
B) so driving current including an AC component through at least the first coil as to drive the bob in at least the first direction through fluid contained by the sample well;
C) sensing a signal that the AC component driven through one of the coils causes in the other of the coils by mutual inductance;
D) generating a sensor output representative thereof, and
E) generating from the sensor output a characterizer output that indicates at least the shear stress on the fluid as a function of the shearing that the fluid undergoes.

28. A method of fluid characterization that includes:
A) providing a ferromagnetic-bob-type instrument that includes:
i) a sample well;
ii) a ferromagnetic bob disposed in the sample well for reciprocation in first and second directions along a bob path therethrough; and
iii) first and second coils so disposed with respect to the sample well that current driven through the first coil results in magnetic force that tends to drive the bob in the first direction, that current driven through the second coil results in magnetic force that tends to drive the bob in the second direction, and that mutual inductance between the coils depends on the bob's position;
B) so driving current including an AC component through at least the first coil as to drive the bob in at least the first direction through fluid contained by the sample well;
C) sensing a signal that the AC component driven through one of the coils causes in the other of the coils by mutual inductance;
D) generating a sensor output representative thereof, and
E) generating from the sensor output a characterizer output that indicates at least how sensitive the fluid's viscosity is to shear rate.

* * * * *